United States Patent
Magno (12) 
(10) Patent No.: US 11,195,676 B2
(45) Date of Patent: Dec. 7, 2021

(54) ELECTRONIC SWITCH MECHANISM

(71) Applicant: Gyrus ACMI Inc., Southborough, MA (US)

(72) Inventor: Joey D. Magno, Cordova, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 0 days.

(21) Appl. No.: 16/093,989

(22) PCT Filed: Apr. 18, 2016

(86) PCT No.: PCT/US2016/028086
§ 371 (c)(1),
(2) Date: Oct. 16, 2018

(87) PCT Pub. No.: WO2017/184107
PCT Pub. Date: Oct. 26, 2017

(65) Prior Publication Data
US 2019/0108952 A1    Apr. 11, 2019

(51) Int. Cl.
*H01H 13/14* (2006.01)
*H01H 13/08* (2006.01)
(Continued)

(52) U.S. Cl.
CPC ............. *H01H 13/14* (2013.01); *A61B 18/14* (2013.01); *H01H 13/063* (2013.01);
(Continued)

(58) Field of Classification Search
CPC ................ H01H 13/14; H01H 13/702; H01H 2009/048; H01H 9/04; H01H 13/06;
(Continued)

(56) References Cited

U.S. PATENT DOCUMENTS 4,536,625 A * 8/1985 Bebie .................. H01H 13/702
                                                                200/339
4,618,754 A    10/1986 Gross ........................ 200/159 B
(Continued)

FOREIGN PATENT DOCUMENTS

CN    105451676 A1    3/2016
CN    109074981 A    12/2018
(Continued)

OTHER PUBLICATIONS

"Chinese Application Serial No. 201680084654.4, Office Action dated Jan. 20, 2020", w/ English Translation, 17 pgs.
(Continued)

*Primary Examiner* — Ahmed M Saeed
(74) *Attorney, Agent, or Firm* — Schwegman Lundberg & Woessner, P.A.

(57) ABSTRACT

A switch mechanism (12) includes a housing (16, 18) with a fenestration (21), a switch element (22) held in the housing, and a membrane switch held in the fenestration. The membrane switch includes a flexible membrane (20) and a rigid rib (26). The rib is constrained to linear movement by guides (37, 38) in the housing so that contact with the membrane causes the membrane to deform and the rib to translate to actuate the switch element.

15 Claims, 5 Drawing Sheets

(51) Int. Cl.
*H01H 21/10* (2006.01)
*H01H 13/06* (2006.01)
*H01H 21/08* (2006.01)
*A61B 18/14* (2006.01)
*H01H 21/24* (2006.01)
*A61B 18/00* (2006.01)
*A61B 17/00* (2006.01)
*H01H 13/52* (2006.01)

(52) U.S. Cl.
CPC .......... *H01H 13/08* (2013.01); *H01H 21/085* (2013.01); *H01H 21/10* (2013.01); *H01H 21/24* (2013.01); *A61B 2017/00367* (2013.01); *A61B 2018/00178* (2013.01); *A61B 2018/00916* (2013.01); *A61B 2018/00952* (2013.01); *H01H 13/52* (2013.01); *H01H 2217/01* (2013.01); *H01H 2217/048* (2013.01); *H01H 2221/002* (2013.01); *H01H 2221/016* (2013.01); *H01H 2221/088* (2013.01); *H01H 2223/003* (2013.01); *H01H 2227/016* (2013.01); *H01H 2233/098* (2013.01); *H01H 2300/014* (2013.01)

(58) Field of Classification Search
CPC ............. H01H 13/08; H01H 2215/008; H01H 2219/04; H01H 2209/074; H01H 2221/002; H01H 2221/084; H01H 21/085; H01H 21/24; H01H 21/10; H01H 2233/098; H01H 2223/003; H01H 2221/088; H01H 13/52; H01H 2227/016; H01H 2217/01; H01H 2217/048; H01H 2300/014; A61B 18/14; A61B 2017/00367
See application file for complete search history.

(56) References Cited

U.S. PATENT DOCUMENTS

| | | | |
|---|---|---|---|
| 5,376,765 A | 12/1994 | Holmes et al. | 200/344 |
| 6,093,900 A * | 7/2000 | Wisskirchen | B29C 45/1671 200/298 |
| 6,303,887 B1 | 10/2001 | Ando | 200/512 |
| 6,331,686 B1 | 12/2001 | Rogatschnig | 200/302.2 |
| 6,331,986 B1 | 12/2001 | Mitra et al. | |
| 6,880,989 B2 | 4/2005 | Sotome | 396/502 |
| 6,911,608 B2 | 6/2005 | Levy | 200/5 A |
| 6,956,180 B1 * | 10/2005 | Su | G06F 1/1626 200/302.1 |
| 6,998,554 B2 | 2/2006 | Shimoda et al. | 200/341 |
| 2002/0046938 A1 | 4/2002 | Donofrio et al. | 200/302.1 |
| 2006/0077777 A1 | 4/2006 | Fried | 369/30.85 |
| 2006/0256510 A1 * | 11/2006 | Nakasono | H01H 13/06 361/679.02 |
| 2011/0284352 A1 * | 11/2011 | Kitahara | H01H 13/06 200/341 |
| 2013/0140164 A1 | 6/2013 | Chen | 200/5 A |
| 2015/0335347 A1 | 11/2015 | Hirai et al. | A61B 17/320092 |

FOREIGN PATENT DOCUMENTS

| | | |
|---|---|---|
| CN | 109074981 B | 7/2020 |
| DE | 1 780 679 | 1/1959 |
| DE | 1780679.8 U | 1/1959 |
| EP | 0 911 844 A2 | 4/1999 |
| EP | 1 199 733 A2 | 4/2002 |
| EP | 1 739 696 A2 | 1/2007 |
| EP | 2 282 316 A1 | 2/2011 |
| EP | 3 005 964 A1 | 4/2016 |
| EP | 3446323 A1 | 2/2019 |
| JP | S-56160726 A | 12/1981 |
| JP | H-11-111099 A | 4/1999 |
| JP | 2002248111 A | 9/2002 |
| JP | 5865723 B2 | 2/2016 |
| WO | WO-2014196419 A1 | 2/2017 |
| WO | WO-2017184107 A1 | 10/2017 |

OTHER PUBLICATIONS

"Chinese Application Serial No. 201680084654.4, Office Action dated Apr. 30, 2019", w/ English Translation, 17 pgs.

"Chinese Application Serial No. 201680084654.4, Office Action dated Sep. 25, 2019", w/ English Translation, 15 pgs.

"Chinese Application Serial No. 201680084654.4, Response filed Mar. 30, 2020 to Office Action dated Jan. 20, 2020", with machine translation, 19 pgs.

"Chinese Application Serial No. 201680084654.4, Response filed Dec. 10, 2019 to Office Action dated Sep. 25, 2019", with machine translation, 17 pgs.

"International Application Serial No. PCT/US2016/028086, International Preliminary Report on Patentability dated Nov. 1, 2018", 8 pgs.

"International Application Serial No. PCT/US2016/028086, International Search Report dated Nov. 25, 2016", 5 pgs.

"International Application Serial No. PCT/US2016/028086, Written Opinion dated Nov. 25, 2016", 6 pgs.

"Chinese Application Serial No. 201680084654.4, Response filed Sep. 10, 2019 to Office Action dated Apr. 30, 2019", with English translation of claims, 12 pgs.

"European Application Serial No. 16719671.6, Response to Communication pursuant to Rules 161(1) and 162 EPC filed Mar. 12, 2019", 28 pgs.

"European Application Serial No. 16719671.6, Communication Pursuant to Article 94(3) EPC dated Oct. 4, 2021", 4 pgs.

\* cited by examiner

ELECTRONIC SWITCH MECHANISM

This patent application is a U.S. National Stage application of International Patent Application Number PCT/US2016/028086 filed Apr. 18, 2016, which is hereby incorporated by reference in its entirety.

FIELD

The present disclosure relates to an electronic switch mechanism. More specifically, the present disclosure relates to an electronic switch mechanism for an electrosurgical instrument.

BACKGROUND

The statements in this section merely provide background information related to the present disclosure and may not constitute prior art.

Typical switches for electrosurgical instruments, as well as other non-medical devices, include one or more tactile push buttons to activate the instrument. For example, certain instruments employ one button for a left-handed operator and a second button for a right-handed operator. Among the literature that can pertain to this technology include, for example, the following patent documents and published patent applications: U.S. Pat. Nos. 4,618,754; 5,376,765; 6,303,887; 6,880,989; 6,911,608; 6,998,554; and U.S. Patent Publication No. 2013/0140164, the entire contents of which are incorporated herein by reference for all purposes.

Accordingly, it would be desirable for an instrument to include a switch mechanism that accommodates ambidextrous operation of the instrument.

SUMMARY

The present disclosure provides an electronic switch mechanism. In various arrangements, the switch mechanism is associated with an electrosurgical instrument. The switch mechanism has two or more buttons or tabs to enable a medical practitioner to actuate the instrument. More specifically, the two or more buttons or tabs are configured to allow the medical practitioner to operate the instrument with either hand. That is, the medical practitioner can use his/her fingers or thumbs from either hand to provide ambidextrous operation of the instrument.

Accordingly, pursuant to one aspect of the present invention, a switch mechanism includes a housing with a fenestration, a switch element held in the housing, and a membrane switch held in the fenestration. The membrane switch includes a flexible membrane and a rigid rib. The rib is constrained to linear movement by guides in the housing so that contact with the membrane causes the membrane to deform and the rib to translate to actuate the switch element.

This aspect of the present invention can be further characterized by one or any combination of the features described herein, such as: the housing is a handpiece; the switch mechanism is on a center plane of the handpiece; the membrane supports off center activation of the switch mechanism; the membrane supports off center activation by about 30°; the membrane is insert molded; and the switch mechanism is arranged to provide ambidextrous operation of the switch mechanism.

Accordingly, pursuant to another aspect of the present invention, a switch mechanism includes a housing with a fenestration, a switch element held in the housing, and a membrane switch held in the fenestration. The membrane includes a flexible membrane and a rigid rib. The rib is constrained so that contact with the membrane causes the membrane to deform and the rib to move to actuate the switch element.

The foregoing aspect of the present invention can be further characterized by one or any combination of the features described herein, such as: the rib is constrained to linear movement by guides in the housing so that contact with the membrane causes the membrane to deform and the rib to translate to actuate the switch element; the rib is constrained to pivotal movement by fulcrums in the housing so that contact with the membrane causes the membrane to deform and the rib to rotate about one of the fulcrums to actuate the switch element; the housing is a handpiece and the switch mechanism is on a center plane of the handpiece and wherein the membrane supports off center activation of the switch mechanism; the membrane is insert molded; and the switch mechanism is arranged to provide ambidextrous operation of the switch mechanism.

Accordingly, pursuant to yet another aspect of the present invention, a switch mechanism includes a housing with a fenestration, a switch element held in the housing, and a membrane switch held in the fenestration. The membrane switch includes a flexible membrane and a rigid rib. The rib is constrained to pivotal movement by fulcrums in the housing so that contact with the membrane causes the membrane to deform and the rib to rotate about one of the fulcrums to actuate the switch element.

The foregoing aspect of the present invention may be further characterized by one or any combination of the features described herein, such as: the housing is a handpiece; the switch mechanism is on a center plane of the handpiece; the membrane supports off center activation of the switch mechanism; the membrane supports off center activation by about 300; the membrane is insert molded; and the switch mechanism is arranged to provide ambidextrous operation of the switch mechanism.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Figure 1:
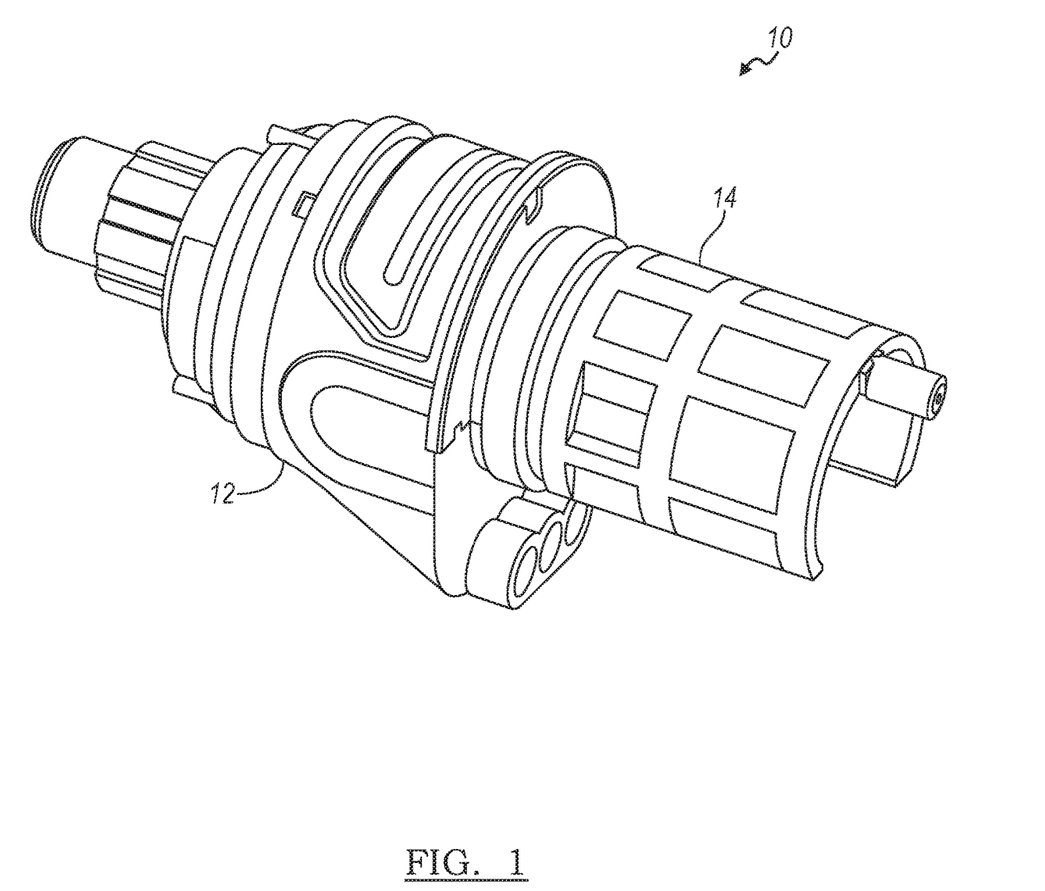
FIG. 1 is a perspective view of a switch mechanism with a portion of a handle in accordance with the principles of the present invention.

Referring now to FIG. 1, a handpiece for an electrosurgical instrument embodying the principles of the present invention is illustrated therein and designated at 10. The handpiece 10 includes an electronic switch mechanism 12 attached to a handle 14. The switch mechanism and the handle 14 can be separate units attached to each other or a single integral unit.

Figure 2:
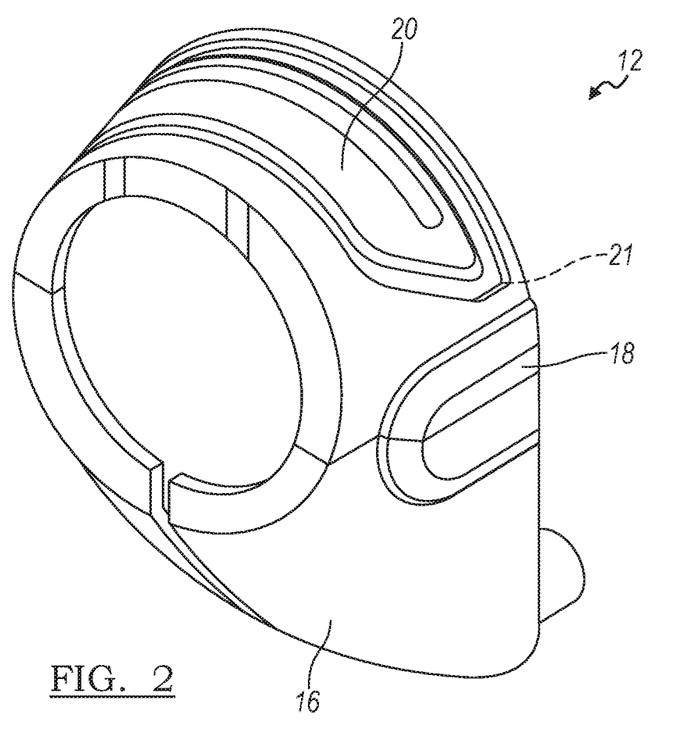
FIG. 2 is an isolated view of the switch mechanism shown in FIG. 1.
Figure 3:
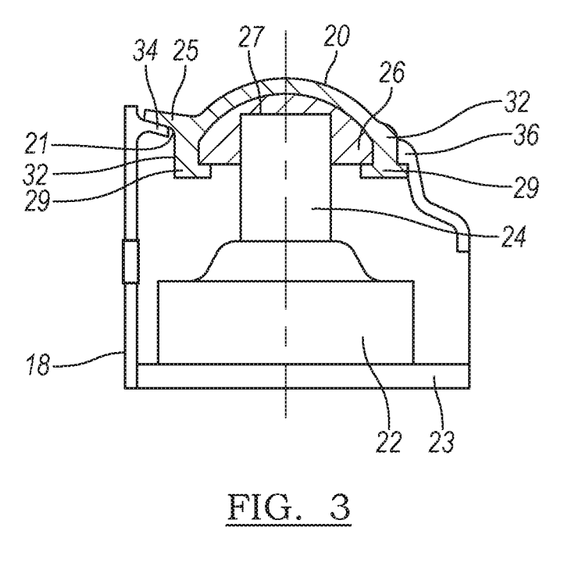
FIG. 3 is a side cross-sectional view of the switch mechanism shown in FIG. 1.

Referring further to FIGS. 2 and 3, the electronic switch mechanism 12 includes a lower housing 16 and an upper housing 18. The upper housing 18 includes an opening or fenestration 21 that holds a membrane switch with a membrane 20 and a rigid rib 26. The rigid rib 26 includes rib extensions 28 as shown in FIGS. 4 and 5 to provide additional rigidity to the rigid rib 26.

The upper housing 18 includes an interior platform or member 23 that supports a switch 22. The switch 22 includes an upper extension or button 24 that engages with the rigid rib 26 in a region 27. The membrane 20 includes extensions 32 with tab portions 29 and further includes an upper tab portion 25. As such, one of the tab portions 29 latches underneath the rigid rib 26 and a lip 36 of the upper housing 18, and the other tab portion 29 latches underneath the rigid rib 26 while the upper tab portion 25 engages with a lip 34 of the upper housing 18. Accordingly, the engagement of the lips 34 and 36 of the housing 18 with the membrane 20 secures the membrane 20 in the fenestration 21.

Figure 4:
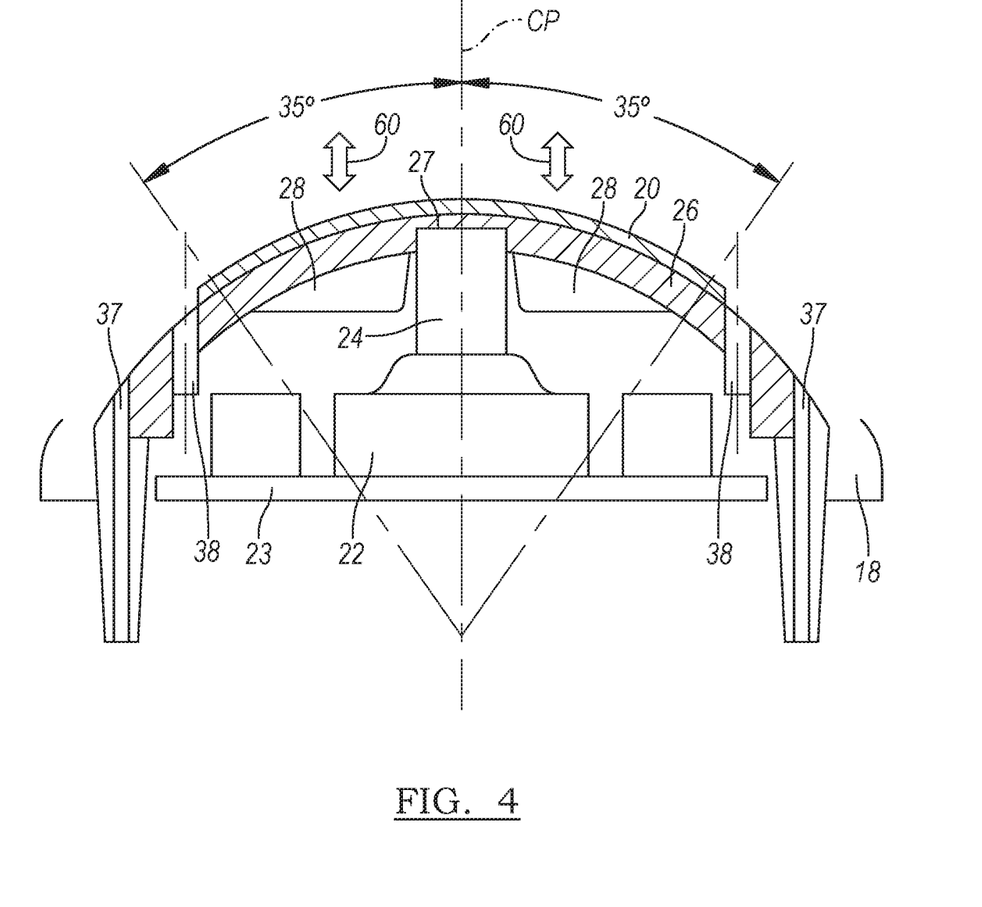
FIG. 4 is a front cross-sectional view of the switch mechanism shown in FIG. 1.
Figure 5:
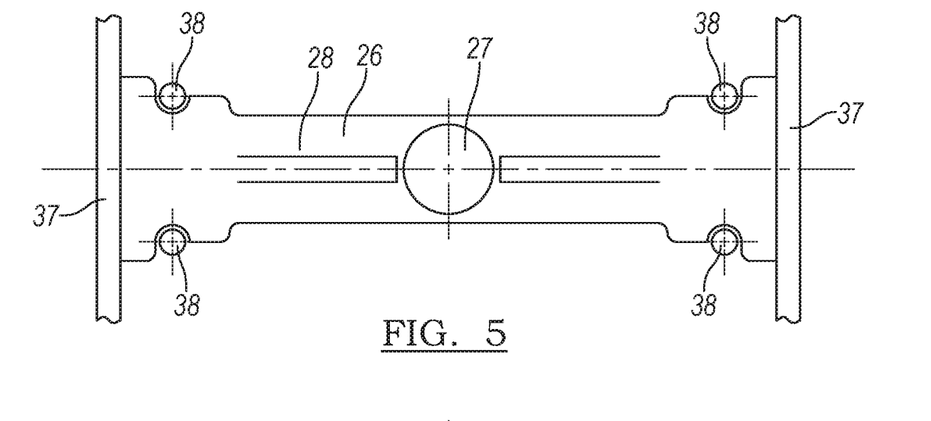
FIG. 5 is an interior top view of the switch mechanism shown in FIG. 1.

Referring in particular to now FIGS. 4 and 5, the lateral most extent of the rigid rib 26 slide up and down along inner walls 37 of the upper housing 18. A set of posts 38 positioned on both sides of the rigid rib 26 engage in a manner with the rigid rib 26 to provide guidance to the rigid rib 26 as it follows the walls 37. Hence, the walls 37 and the posts 38 enable the rigid rib 26 to provide vertical actuation of the switch 22. Specifically, as a medical professional presses on the membrane 20, as indicated by the downward portions of the arrows 60, contact between the membrane 20 and the rigid rib 26 causes the rigid rib 26 to press against the button 24, which, in turn, actuates the switch 22. After pressure is removed from the membrane 20, the membrane along with the rigid rib 26 springs back and retains its original shape as indicated by the upper portions of the arrows 60 so that the switch mechanism 12 returns to its original un-actuated position.

The switch 22 in certain arrangements controls the activation of an energy source. For example, if the switch mechanism 12 is associated with an electrosurgical instrument with electrodes, the switch mechanism may control the operation of a radiofrequency (RF) energy source electrically connected to the instrument. Hence, when a medical profession presses and actuates the switch mechanism 12, electrical energy is delivered to the electrodes to treat, for example, tissue of a patient. The associated instrument can be forceps that coagulate or cut the tissue. The instrument can be a monopolar instrument that only requires one electrode that interacts with a neutral electrode, which is likewise connected to the body of a patient. Alternatively, the instrument can be a bipolar electrosurgical instrument with two electrodes (a distal electrode and a proximal electrode). A RF voltage with different potentials is applied to such bipolar instruments so that a current passes from one electrode to the other electrode through the tissue, thereby heating the tissue to coagulate or cut the tissue.

In some arrangements, the membrane 20 is insert molded from a flexible low-durometer material. In the arrangement shown in FIG. 4, the membrane 20 has an arc span of approximately 70°, for example, an arc span of approximately 35° from each side of a center plane, CP. Accordingly, if a force is applied to the membrane 20 anywhere in this 70° arc span, the resulting displacement of the membrane 20 is translated into vertical motion of the rigid rib 26 to push the button 24, which in turn actuates the instrument associated with the switch mechanism 12. In other arrangements, the arc span of the membrane 20 can be greater than or less than 70°.

Figure 6:
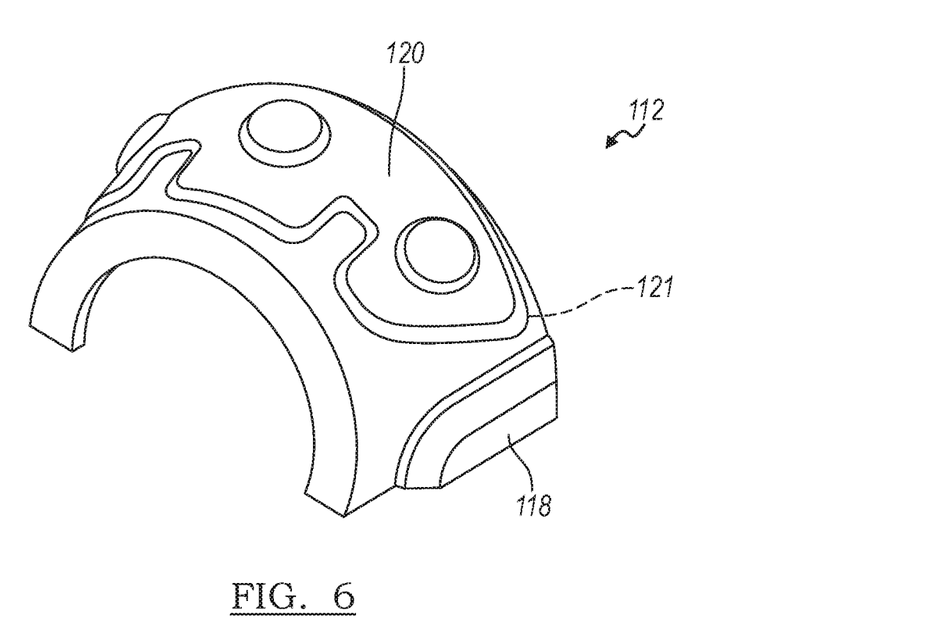
FIG. 6 is a perspective view of alternative switch mechanism in accordance with the principles of the present invention.

Turning now to FIG. 6, there is shown an alternative switch mechanism 112. The switch mechanism 112 includes a lower housing similar to the previously described lower housing for the switch mechanism 12 as well as an upper housing 118. The upper housing 118 includes an opening or fenestration 121, which holds a membrane switch with a membrane 120.

Figure 7:
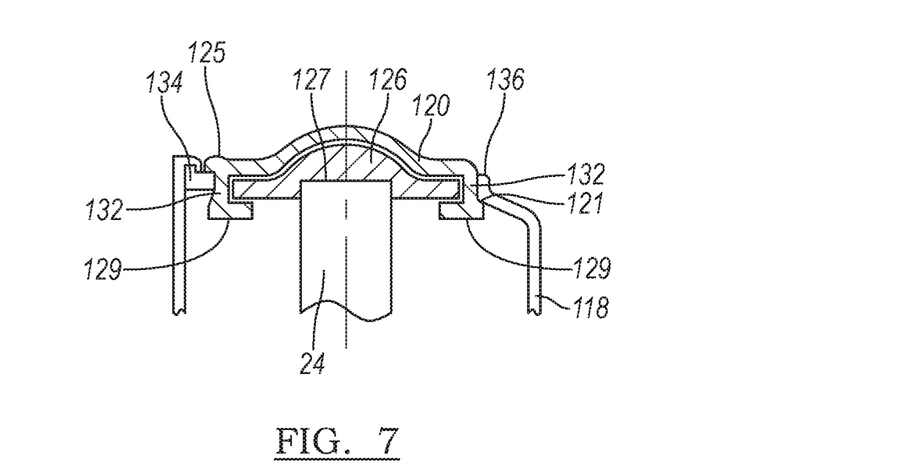
FIG. 7 is a side cross-sectional view of the switch mechanism shown in FIG. 6.
Figure 8:
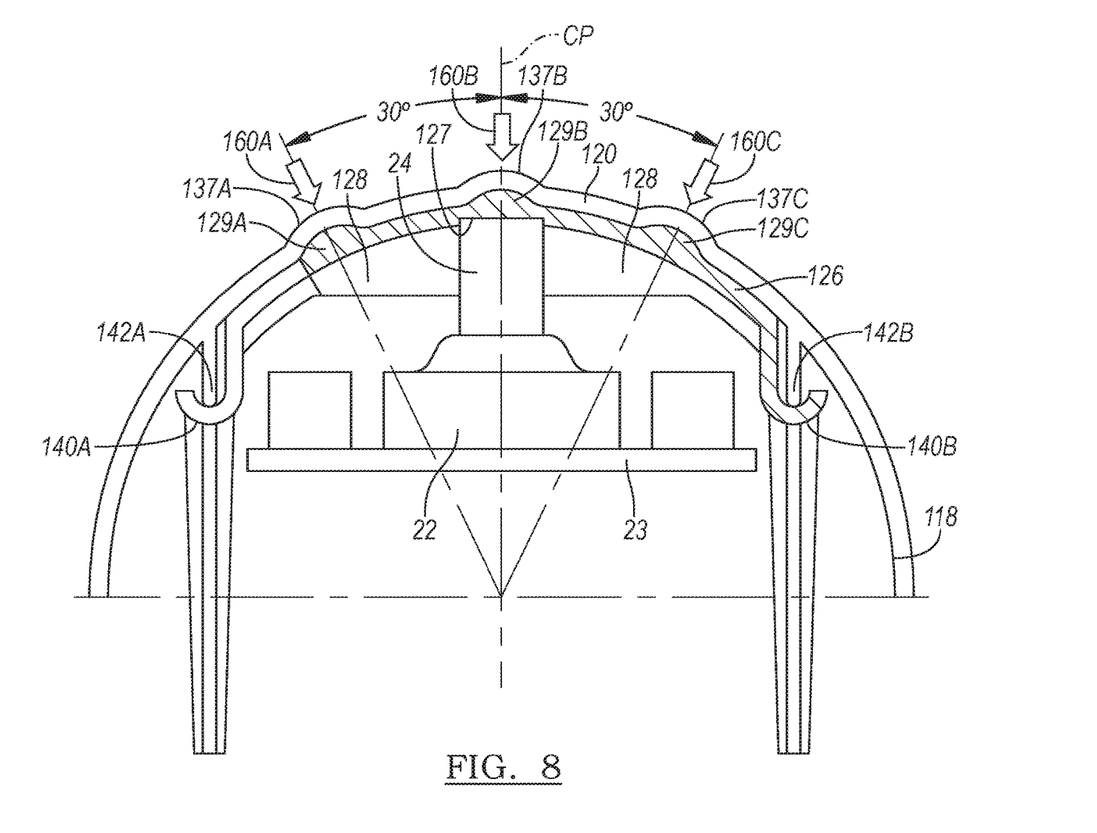
FIG. 8 is a front cross-sectional view of the switch mechanism shown in FIG. 6.
Figure 9:
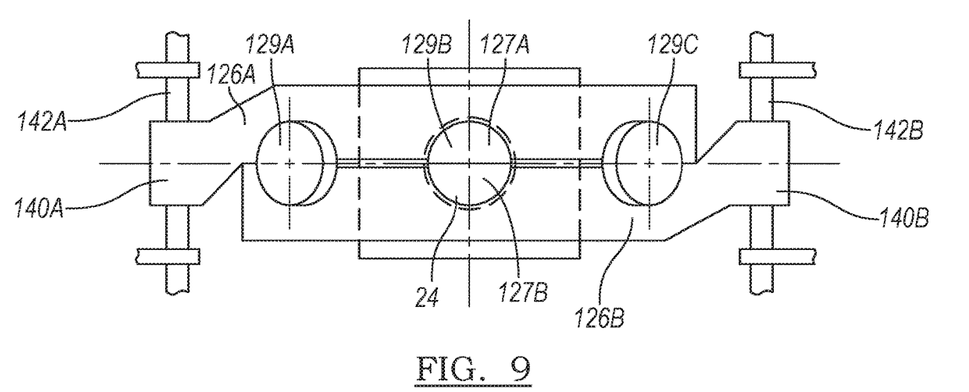
FIG. 9 is an interior top view of the switch mechanism shown in FIG. 6.

Referring further to FIGS. 7 and 8, the membrane switch further includes a pair of rigid ribs 126, shown as rigid ribs 126A and 126B in FIG. 9, and the rigid ribs 126 include rib extensions 128 to provide additional rigidity to the rigid ribs 126. The upper housing 118 holds a switch 22 on a platform 23. The switch 22 includes an upper extension or button 24 that engages with the rigid ribs 126 in a region 127. More specifically, as shown in FIG. 9, the rigid rib 126A engages with the two button 24 in a region 127A, and the rigid rib 126B engages with the button 24 in a region 127B. The membrane 20 includes extensions 132 with tab portions 129 and further includes an upper tab portion 125. As such, one of the tab portions 129 latches underneath the rigid ribs 126 and a lip 136 of the upper housing 118. The other tab portion 129 latches underneath the rigid ribs 126 while the upper tab portion 125 engages with a lip 134 of the upper housing 118. Accordingly, the engagement of the lips 134 and 136 with the membrane 120 secures the membrane 120 in the fenestration 121.

The rigid ribs 126 include set of protrusions or bumps 129A, 129B, and 129C. More specifically, the bump 129A is associated with the rigid rib 126B, the bump 129C is associated with the rigid rib 126A, and the bump 129B is associated with both rigid ribs 126A and 126B. The membrane 120 includes a set of protrusions or bumps 137A, 137B, and 137C that are in contact with the bumps 129A, 129B, and 129C, respectively. The location of the bumps 129A, 129B, and 129C provides tactile information to the medical professional as to where the medical professional's fingers and/or thumbs are located with respect to the membrane 120.

Referring also to FIG. 9, the lateral most extent 140A and 140B of the rigid ribs 126A and 126B, respectively, engage with respective fulcrums 142A and 142B associated with the upper housing 118. Accordingly, as a medical professional presses on the lateral portions of the membrane 120, as indicated by the arrows 160A and 160C, contact between the membrane 120 and the rigid rib 126A or 126B causes the rigid rib 126A or 126B to pivot about the respective fulcrum 142A or 142B. That is, the rigid ribs 126A and 126B pivot about the fulcrums 142A and 142B independently from each other. Accordingly, pressure on the bump 137A presses the bump 137A against the bump 129A of the rigid rib 126B such that the rigid rib 126B pivots about the fulcrum 142B and presses against the button 24 in the region 127B, which, in turn, actuates the switch 22. And pressure on the bump 137C presses the bump 137C against the bump 129C of the rigid rib 126A such that the rigid rib 126A pivots about the fulcrum 142A and presses against the button 24 in the region 127A, which, in turn, actuates the switch 22. Note that downward pressure in the medial region of the membrane 120, as indicated by the arrow 160B, causes the lateral portions 140A and 140B of the rigid ribs 126A and 126B to translate vertically downward away from the fulcrums 142A and 142B. This downward motion causes the rigid ribs 126A and 126B to press against the button 24 in the regions 127A and 127B, which actuates the switch 22 of the switch mechanism 112. After pressure is removed from the membrane 120, the membrane 120, along with the rigid ribs 126A and 126B, springs back and retains its original shape so that the switch mechanism 112 returns to its original un-actuated position.

The switch 22 in certain arrangements controls the activation of an energy source. For example, if the switch mechanism 112 is associated with an electrosurgical instrument with bipolar electrodes, the switch mechanism may control the operation of a radiofrequency (RF) energy source electrically connected to the instrument. Hence, when a medical profession presses actuates the switch mechanism 112, electrical energy is delivered to the electrodes to treat, for example, tissue. The associated instrument can be forceps that coagulate or cut the tissue. The instrument can be a monopolar instrument that only requires one electrode that interacts with a neutral electrode, which is likewise connected to the body of a patient. Alternatively, the instrument can be a bipolar electrosurgical instrument with two electrodes (a distal electrode and a proximal electrode). A RF voltage with different potentials is applied to such bipolar instruments so that a current passes from one electrode to the other electrode through the tissue, thereby heating the tissue to coagulate or cut the tissue.

In some arrangements, the membrane 120 is insert molded from a flexible low-durometer material. In the arrangement shown in FIGS. 6 through 9, the arc span between the bumps 160A and 160C of the membrane 120 is approximately 60°, that is, an arc span of approximately 30° from each side of a center plane, CP. Accordingly, if a force is applied to the membrane 120 anywhere in this 600 arc span, the resulting displacement of the membrane 120 is translated into motion of the rigid ribs 126A or 126B in the regions 127A or 127B to push the button 24, which in turn actuates the instrument associated with the switch mechanism 112. In other arrangements, the arc span between the bumps 160A and 160C can be greater than or less than 60°.

The description of the invention is merely exemplary in nature and variations that do not depart from the gist of the invention are intended to be within the scope of the invention. Such variations are not to be regarded as a departure from the spirit and scope of the invention.

What is claimed is:

1. A switch mechanism comprising:
   a housing, where the housing comprises a fenestration, a lip, and a plurality of guides;
   a switch element held in the housing; and
   a membrane switch, the membrane switch being held in the fenestration and including a flexible membrane, a rigid rib, and a button extending between the rigid rib and the switch element, the flexible membrane including:
   a first side defining an outer surface of the switch mechanism and an opposing second side, the rigid rib disposed within the housing and adjacent to the second side of the flexible membrane; and
   a tab portion configured to engage with the housing lip and the rigid rib;
   wherein the rigid rib is constrained to linear movement along the plurality of guides so that a contact with the flexible membrane is configured to cause the flexible membrane to deform and the rigid rib to slide along the plurality of guides and provide a translational planar motion displacement of the rigid rib relative to the plurality of guides to actuate the switch element via the button.

2. The switch mechanism of claim 1 wherein the housing is a handpiece.

3. The switch mechanism of claim 2 wherein the switch mechanism is on a center plane of the handpiece.

4. The switch mechanism of 3 wherein the flexible membrane supports off center activation of the switch mechanism.

5. The switch mechanism of claim 4 wherein the flexible membrane supports off center activation by about 30°.

6. The switch mechanism of claim 1 wherein the flexible membrane is insert molded.

7. The switch mechanism of claim 1 wherein the switch mechanism is arranged to provide ambidextrous operation of the switch mechanism.

8. A switch mechanism comprising:
   a housing, where the housing comprises a fenestration, a lip, and a plurality of guides;
   a switch element held in the housing; and
   a membrane switch, the membrane switch being held in the fenestration and including a flexible membrane, a rigid rib, and a button extending between the rigid rib and the switch element, the flexible membrane including:
   a first side defining an outer surface of the switch mechanism and an opposing second side, the rigid rib disposed within the housing and adjacent to the second side of the flexible membrane; and
   a tab portion configured to engage with the housing lip and the rigid rib, wherein the rigid rib includes a plurality of recesses that receive and directly contact the plurality of guides in a mating relationship; and
   wherein the rigid rib is constrained to translational planar motion displacement of the rigid rib along the plurality of guides so that a contact with the flexible membrane is configured to cause the flexible membrane to deform and the rigid rib to move to actuate the switch element via the button.

9. The switch mechanism of claim 8 wherein the rib is constrained to linear movement by the plurality of guides in the housing so that contact with the flexible membrane causes the flexible membrane to deform and the rigid rib to slide along the plurality of guides to actuate the switch element.

10. The switch mechanism of claim 8 wherein the housing is a handpiece and the switch mechanism is on a center plane of the handpiece and wherein the flexible membrane supports off center activation of the switch mechanism.

11. The switch mechanism of claim 8 wherein the flexible membrane is insert molded.

12. The switch mechanism of claim 8 wherein the switch mechanism is arranged to provide ambidextrous operation of the switch mechanism.

13. A switch mechanism comprising:
a housing, where the housing comprises a fenestration and a plurality of guides;
a switch element held in the housing; and
a membrane switch, the membrane switch being held in the fenestration and including a flexible membrane, a rigid rib, and a button extending between the rigid rib and the switch element, the flexible membrane including a first side defining an outer surface of the switch mechanism and an opposing second side, the rigid rib disposed within the housing and adjacent to the second side of the flexible membrane;
the rigid rib being constrained with the housing such that, based upon contact with the flexible membrane by a user, the rigid rib is constrained to pivotal movement by fulcrums in the housing such that the rigid rib moves relative to at least one of the guides to allow the flexible membrane to deform and the rigid rib to move relative to housing, to allow a displacement of the rigid rib along the at least one guide, to actuate the switch element via the button, wherein the rigid rib is constrained by the fulcrums such that contact with the flexible membrane causes the flexible membrane to deform and the rigid rib to rotate about one of the fulcrums to actuate the switch element.

14. The switch mechanism as claimed in claim 13 where the rigid rib slides relative to the at least one guide.

15. The switch mechanism as claimed in claim 13 where the rib is constrained to linear movement by guides in the housing so that contact with the flexible membrane causes the flexible membrane to deform and the rib to translate to actuate the switch element.

\* \* \* \* \*

UNITED STATES PATENT AND TRADEMARK OFFICE
CERTIFICATE OF CORRECTION

| | | |
|---|---|---|
| PATENT NO. | : 11,195,676 B2 | Page 1 of 1 |
| APPLICATION NO. | : 16/093989 | |
| DATED | : December 7, 2021 | |
| INVENTOR(S) | : Joey D. Magno | |

It is certified that error appears in the above-identified patent and that said Letters Patent is hereby corrected as shown below:

In the Claims

In Column 6, Line 20, in Claim 4, delete "of 3" and insert --of claim 3-- therefor Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*